US00PP36930P2

(12) United States Plant Patent
van Geest

(10) Patent No.: US PP36,930 P2
(45) Date of Patent: Sep. 2, 2025

(54) ***FICUS* PLANT NAME 'ESFIMO'**

(50) Latin Name: ***Ficus elastica* Roxb**
Varietal Denomination: ESFIMO

(71) Applicant: J. Van Geest Holding B.V., 's Gravenzande (NL)

(72) Inventor: Jan van Geest, 's Gravenzande (NL)

(73) Assignee: J. Van Geest Holding B.V., 's Gravenzande (NL)

( * ) Notice: Subject to any disclaimer, the term of this patent is extended or adjusted under 35 U.S.C. 154(b) by 0 days.

(21) Appl. No.: 18/831,361

(22) Filed: Dec. 12, 2024

(51) Int. Cl.
*A01H 5/12* (2018.01)
*A01H 6/00* (2018.01)

(52) U.S. Cl.
USPC ..... Plt./211

(58) Field of Classification Search
USPC ..... Plt./211
See application file for complete search history.

(56) References Cited

PUBLICATIONS https://online.plantvarieties.eu/publicSearch?denomination=ESFIMO Retrieved from the Internet on Mar. 10, 2025; citation for 'ESFIMO'.*

* cited by examiner

*Primary Examiner* — Susan McCormick Ewoldt
(74) *Attorney, Agent, or Firm* — Samuel R. McCoy, Jr.

(57) ABSTRACT

A new and distinct variety of *Ficus* plant named 'ESFIMO' which is characterized by a compact growth habit with broad ovate foliage, cream-colored mature foliage that is flecked with yellow-green and greyed-green and centrally blotched with dark green and greyed-green, and light red main veins that are flecked and striated with light greyed-yellow. 'ESFIMO' exhibits the stability of the previously noted characteristics from generation to generation.

3 Drawing Sheets

Latin name of the genus and species: The Latin name of the genus and species of the novel variety disclosed herein is *Ficus elastica* Roxb.

Variety denomination: The inventive variety of *Ficus* disclosed herein has been given the variety denomination 'ESFIMO'.

BACKGROUND OF THE INVENTION

Parentage: 'ESFIMO' originated as a naturally occurring, whole-plant mutation of *Ficus elastica* 'SCHRIJVERIANA' (Community Plant Variety Rights grant number 101562; not patented in the United States). The inventor discovered the mutation in the summer of 2019 at their commercial greenhouse located in 's-Gravenzande, The Netherlands, growing amongst a cultivated population of 'SCHRIJVERIANA' plants. The mutation was noted for its compact size and smaller, uniquely-colored foliage relative to the parent plant. Said mutated plant subsequently isolated for further evaluation in order to confirm the distinctness and stability of the characteristics first observed.

Asexual Reproduction: Stem cuttings were first used to propagate 'ESFIMO' in September 2019 at a commercial greenhouse in 's-Gravenzande, The Netherlands. Through five subsequent generations of asexual reproduction, the unique features of this cultivar have proven to be stable and true to type.

SUMMARY OF THE INVENTION

The cultivar 'ESFIMO' has not been observed under all possible environmental conditions. In and of itself, the phenotype may be altered somewhat with changes in environment such as temperature, day length, and light intensity, without any variance in the genotype. The following traits have been repeatedly observed and are determined to be the unique characteristics of 'ESFIMO'. These characteristics in combination distinguish 'ESFIMO' as a new and distinct *Ficus* cultivar:

1. *Ficus* 'ESFIMO' exhibits a compact growth habit; and
2. *Ficus* 'ESFIMO' exhibits relatively small broad ovate foliage; and
3. *Ficus* 'ESFIMO' exhibits a juvenile adaxial foliar surface that is colored greyed-yellow, suffused with a mixture of yellow-orange, orange and yellow-green, with dark yellow-green and greyed-green flecking, and large dark green and greyed-green central blotches; and
4. *Ficus* 'ESFIMO' exhibits a mature adaxial foliar surface that is colored with a combination of light yellow, light yellow-green, and white, generally appearing as a cream coloration, with dark yellow-green and greyed-green flecking, and large dark green and greyed-green central blotches; and
5. *Ficus* 'ESFIMO' exhibits mature foliage with light red main veins on the adaxial surface that are irregularly flecked and striated with light greyed-yellow.

BOTANICAL DESCRIPTION OF THE PLANT

Figure 1:
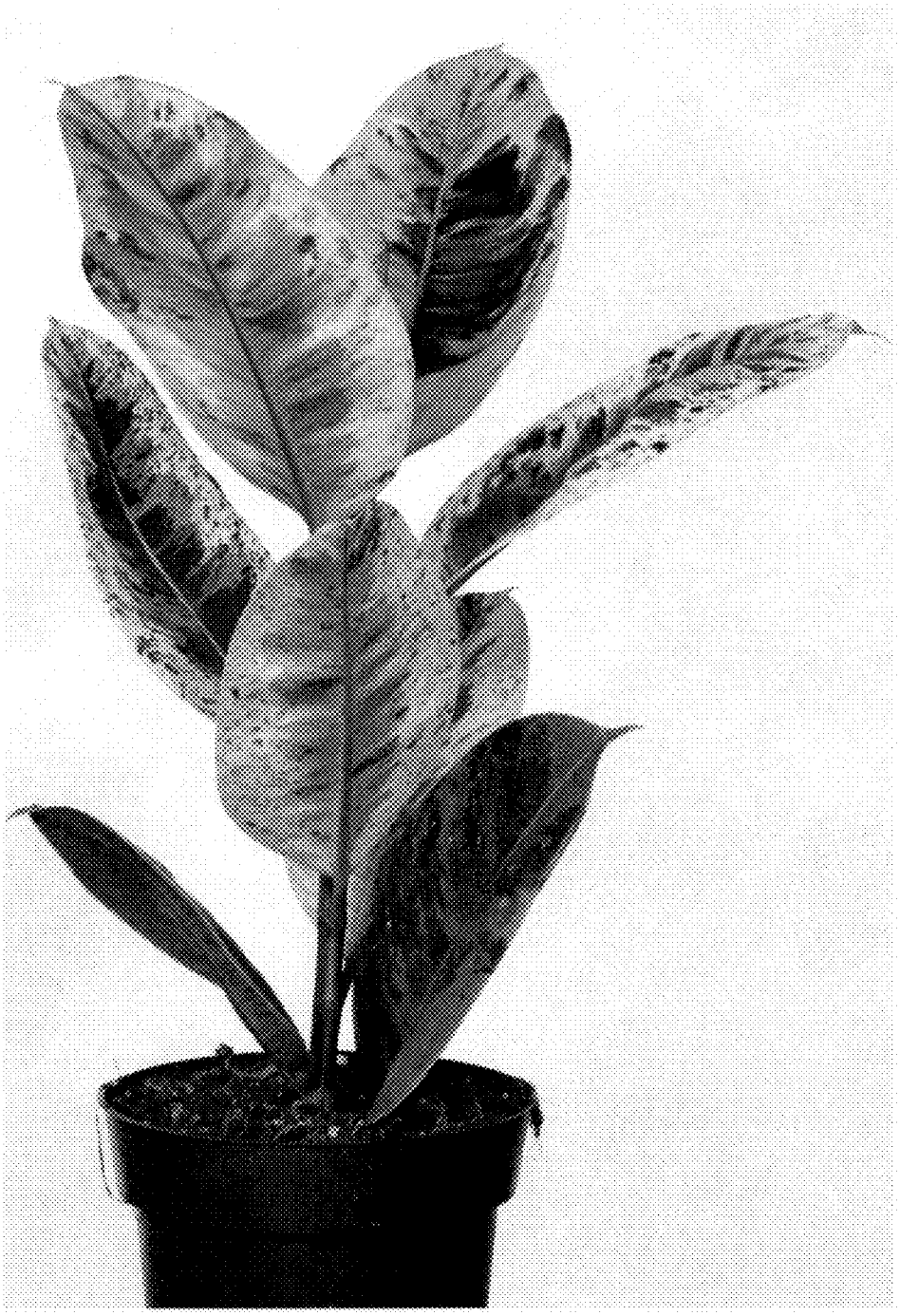
FIG. 1 illustrates, as nearly true as it is reasonably possible to make the same in color photographs of this type, an exemplary plant of 'ESFIMO' grown in a commercial greenhouse in Gravenzande, The Netherlands. This plant is approximately 12 months old, planted in a 12 cm container.
Figure 2:
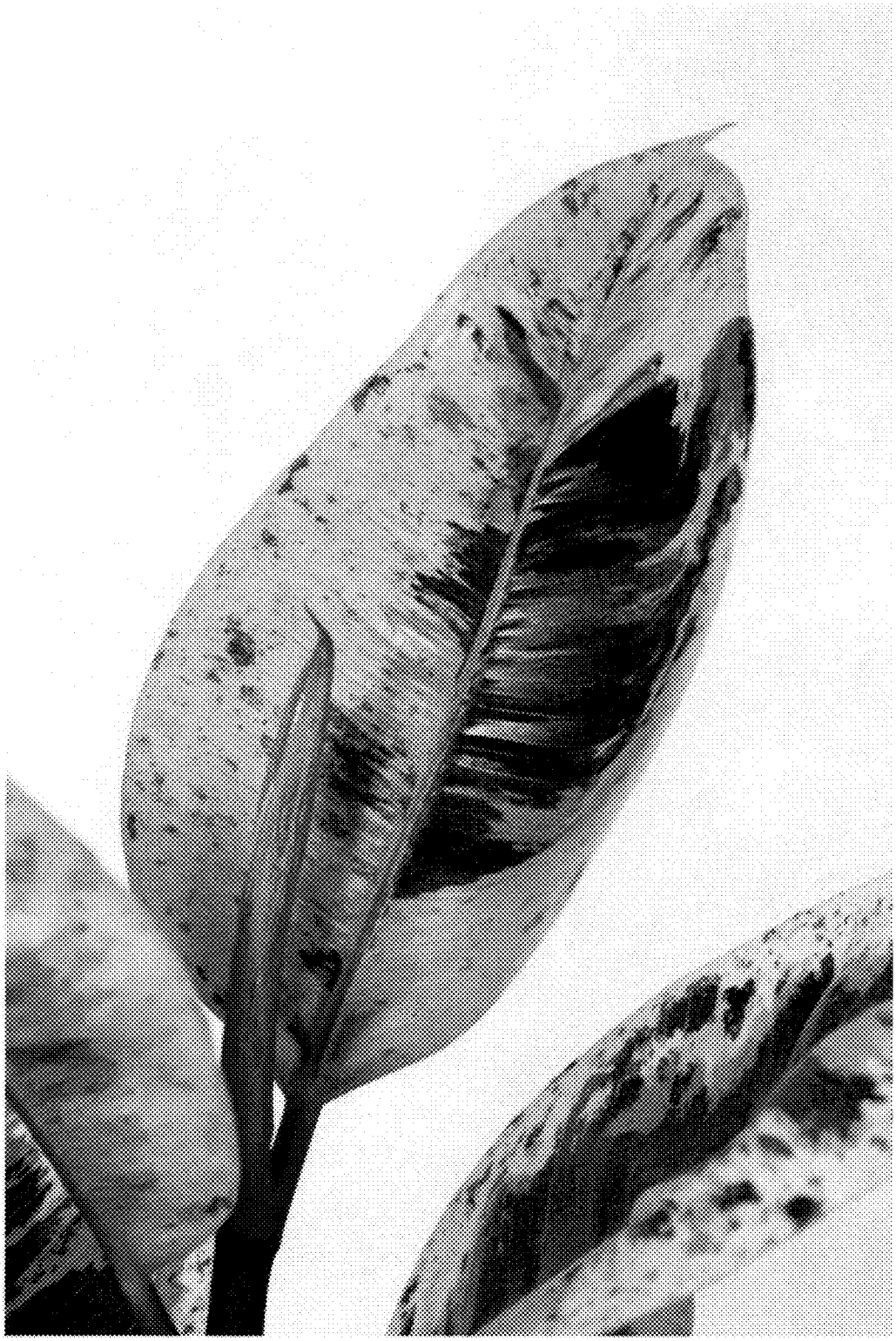
FIG. 2 illustrates, as nearly true as it is reasonably possible to make the same in color photographs of this type, the typical juvenile foliage of 'ESFIMO'.
Figure 3:
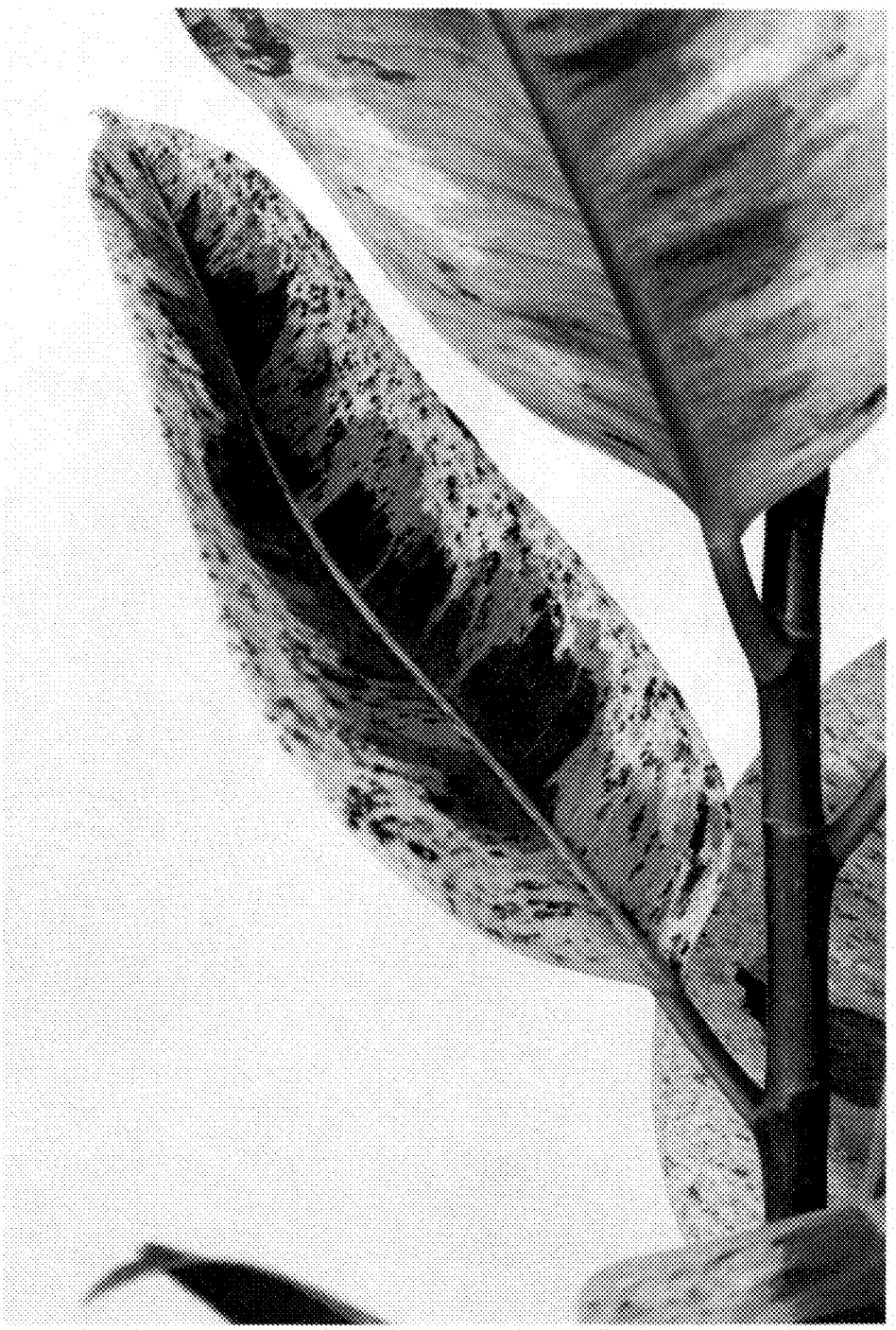
FIG. 3 illustrates, as nearly true as it is reasonably possible to make the same in color photographs of this type, the typical mature foliage of 'ESFIMO'.

The following observations and measurements were made in April of 2021 and describe a sample set of six 12-month-old 'ESFIMO' plants grown in 12 cm nursery pots at a greenhouse in 's-Gravenzande, The Netherlands. The plants were propagated successfully without supplemental fertilizer or pest control measures in a greenhouse with full sun exposure. Water availability was provided by tidal irrigation and no supplemental lighting was used.

Those skilled in the art will appreciate that certain characteristics of the variety 'ESFIMO' will change with time as the plant develops. The variety has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'ESFIMO' as well as comparisons with the parent plant and most similar commercial variety of *Ficus* are provided below.

Plant description:

*Growth habit*.—Broad, upright perennial evergreen.

*Plant profile*.—Obovate to broadly oblong.

*Average height*.—35.2 cm.

*Plant spread*.—31.9 cm.

*Plant vigor*.—Moderately vigorous.

*Propagation type*.—Stem cuttings.

*Time to produce a rooted cutting*.—Approximately 40 days to produce a rooted cutting at approximately 25 degrees Celsius.

*Time to produce a finished plant*.—Approximately 18 weeks to produce a marketable finished plant in a 17 cm pot.

*Pest and pathogen resistance and susceptibility*.—Plants have been observed to be similarly susceptible and resistant to pathogens and pests common to *Ficus* sp.

*Environmental tolerances*.—Adapt to, at least, USDA Zones 10 through 12 and temperatures as high as 40 degrees Celsius; moderate tolerance to rain; low to moderate tolerance to wind.

Root system:

*General*.—Main root with moderately dense branched secondary rooting; roots are slightly fibrous.

*Distribution in the soil profile*.—Moderately deep.

*Diameter of roots*.—1.5 mm.

*Texture*.—Smooth and glabrous.

*Color*.—Greyed-yellow, nearest to RHS 162D.

Stem:

*General branching habit*.—Basally branching main stem; with no lateral branching present. Stems produce milky exudate when damaged.

*Color of developing stems*.—Grey-brown, nearest to RHS N199A.

*Color of mature stems*.—Yellow-green, nearest to RHS 146A.

*Color at internodes*.—Green, nearest to RHS 146A; each internode has a thin radial ring that averages at 0.4 mm in width and is colored greyed-orange, nearest to RHS 176A.

*Color, oldest wood*.—Green, nearest to RHS 137B with axillary striations of greyed- orange, nearest to a combination of RHS 176A and 176B.

*Texture*.—Glabrous and sparsely covered with small lenticels as stems age.

*Luster*.—Slightly glossy.

*Main stem*.—Quantity — 1. Length — 20.4 cm. Diameter — 0.8 cm. Internode length — 3.4 cm. Aspect — Terete. Attitude — Upright; near vertical. Strength — Strong.

Foliage:

*Arrangement*.—Alternate, whorled.

*Division*.—Simple.

*Quantity*.—5 leaves.

*Attitude*.—At an average angle of 60 degrees to the main stem.

*Shape*.—Broad ovate.

*Aspect*.—Slightly to moderately carinate; slightly irregularly concaved.

*Length*.—17.5 cm.

*Width*.—10.0 cm.

*Apex*.—Broad abruptly acute.

*Base*.—Rounded.

*Margin*.—Entire, slightly repand, slightly revolute; unlobed.

*Texture and luster, adaxial surface*.—Glabrous, smooth, and slightly glossy; sparsely covered with small circular glands at the marginal zone. Glands are 0.3 mm in diameter and colored yellow-green, nearest to RHS 150D.

*Texture and luster, abaxial surface*.—Glabrous, smooth, and matte.

*Color*.—Juvenile foliage, adaxial surface — The central zone of the lamina is irregularly blotched with a combination of green and greyed-green, nearest to RHS NN137A, NN137B, N139A, 194A and 194B; the balance of the lamina is colored greyed-yellow, nearest to a combination of RHS 161A and 162A, and suffused with a mixture of a yellow-orange, orange and yellow-green, nearest to RHS 22B, 22C, 26A, 29B and 153D. These same portions of the lamina are also flecked with yellow-green, nearest to a combination of RHS 146A, 146B, 147A and 147B. Juvenile foliage, abaxial surface — Greyed-yellow; nearest to a mixture of RHS 161A and 161B, and suffused with greyed-orange, nearest to RHS N170C; the green and greyed-green blotches on the adaxial surface are visible as a greyed-orange coloration, nearest to RHS 177C and 177D; lightly and flecked with yellow-green; nearest to RHS 147B, 148A and 148B. Mature foliage, adaxial surface — The central zone of the lamina is irregularly blotched with a combination of green, yellow-green and greyed-green, nearest to RHS NN137A, 147A, N189A, and a mixture of 194B, 194C, and 195D; the balance of the lamina is colored with a combination of yellow, yellow-green, and white, nearest to RHS 4D, 150D, and 155A. These same portions of the lamina are also flecked with a combination of yellow-green and greyed-green, nearest to RHS 146A, 147A, 194A, 195A, and 195B. Mature foliage, abaxial surface — Greyed-yellow, nearest to RHS 160D, and suffused with greyed-orange, nearest to a mixture of RHS 197C and 197D; the green, yellow-green and greyed-green blotches on the adaxial surface are visible as a greyed-green coloration, nearest to a mixture of RHS 197C and 197D, with a greyed-orange hue; near 174C and 174D; moderately flecked with yellow-green, nearest to RHS 146A, 146B, 147A and 147B.

*Venation*.—Pattern — Pinnate. Color, adaxial surface — Red, nearest to RHS 36B to 36D; main veins are also flecked and irregularly striped with yellow-green; near 146A and 147A. Color, abaxial surface — Greyed-orange; nearest to RHS 174C and 174D.

*Stipule*.—Arrangement — A single stipule is present at the base of each leaf on the main stem; the stipule envelops the juvenile leaves prior to unfurling and later senesces once the leaf is fully open. Quantity — 1 per leaf. Shape — Lanceolate. Aspect — Concave. Apex — Narrow Acuminate. Base — Broad. Margins — Entire. Length — 10.4 cm. Width — 2.3 cm. Luster and Texture — Both sides are glabrous and slightly glossy. Color, inner surface — Red, nearest to RHS 50D, with greyed-yellow striations, nearest to a combination of RHS 162C and 162D. Color, outer surface — Red, nearest to RHS 47C, with striations on the bottom are darker red, nearest to RHS 47A.

*Petiole*.—Length — 1.9 cm. Diameter — Slightly flattened; the average height is 0.35 cm, and the average width is 0.4 cm. Strength — Strong. Texture — Smooth; glabrous. Luster — Moderately glossy. Color, adaxial surface — Greyed-orange nearest to RHS 174C; longitudinally striped with greyed-green; nearest to a combination of RHS 197A and 197B. Color, abaxial surface — Greyed-orange, nearest to RHS 147C.

Inflorescence: No flowering has been observed to date.

COMPARISON WITH THE PARENT PLANT

Plants of the new cultivar 'ESFIMO' differ from the parent, *Ficus elastica* 'SCHRIJVERIANA', in the following characteristics described in Table 1 below.

TABLE 1

| Characteristic | 'ESFIMO' | 'SCHRIJVERIANA' |
|---|---|---|
| Foliage abundance. | More abundant than 'SCHRIJVERIANA'. | Less abundant than 'ESFIMO'. |
| Foliage size. | 17.5 cm long and 10 cm wide. | Up to 30 cm long and 20 cm wide. |
| General coloration of the mature foliage. | A combination of light yellow, light yellow-green, and white, generally appearing as a cream coloration, with dark yellow-green and greyed-green flecking, and large dark green and greyed-green central blotches. | In between light green-yellow and light yellow-green and flecked with dark green. Occasionally blotched with dark green and greyed-green. |

COMPARISON WITH THE CLOSEST KNOWN COMPARATOR

Plants of the new cultivar 'ESFIMO' are similar to the cultivar, *Ficus* 'ESFIDECLO1', (U.S. Plant Pat. No. 33,409). A comparison of 'ESFIMO' with *Ficus* 'ESFIDECLO1' is described in Table 2 below.

TABLE 2

| Characteristic | 'ESFIMO' | 'ESFIDECLO1' |
|---|---|---|
| Foliage size. | 17.5 cm long and 10 cm wide. | Larger than 'ESFIMO' 18.5 cm long and 13.6 cm wide. |
| General coloration of mature foliage. | A combination of light yellow, light yellow-green, and white, generally appearing as a cream coloration, with dark yellow-green and greyed-green flecking, and large dark green and greyed-green central blotches. | Homogenously dark green. |

That which is claimed is:

1. A new and distinct variety of *Ficus* plant named 'ESFIMO', substantially as described and illustrated herein.

* * * * *